(12) United States Patent
De Boer et al.

(10) Patent No.: US 7,867,938 B2
(45) Date of Patent: Jan. 11, 2011

(54) CATALYTIC OLIGOMERIZATION OF OLEFINIC MONOMERS

(75) Inventors: Eric Johannes Maria De Boer, Amsterdam (NL); Harry Van Der Heijden, Amsterdam (NL); Quoc An On, Amsterdam (NL); Johan Paul Smit, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 1067 days.

(21) Appl. No.: 11/561,812

(22) Filed: Nov. 20, 2006

(65) Prior Publication Data
US 2007/0129583 A1    Jun. 7, 2007

(30) Foreign Application Priority Data
Nov. 21, 2005    (EP) .................................. 05257158

(51) Int. Cl.
*C07C 13/00*    (2006.01)
(52) U.S. Cl. ........................ 502/100; 502/121; 502/102; 502/124; 502/125; 502/103; 585/527; 585/513; 585/514; 585/516; 585/17
(58) Field of Classification Search ........................ None
See application file for complete search history.

(56) References Cited

U.S. PATENT DOCUMENTS

| | | | |
|---|---|---|---|
| 5,198,563 A | 3/1993 | Reagen et al. | 556/57 |
| 5,523,507 A | 6/1996 | Reagen et al. | 585/513 |
| 5,968,866 A | 10/1999 | Wu | 502/155 |
| 6,800,702 B2 | 10/2004 | Wass | 526/124.3 |
| 7,297,832 B2 * | 11/2007 | Blann et al. | 585/527 |
| 2005/0113622 A1 | 5/2005 | Drent et al. | 585/521 |
| 2006/0128910 A1 | 6/2006 | Blann et al. | 526/160 |
| 2006/0173226 A1 | 8/2006 | Blann et al. | 585/511 |
| 2006/0211903 A1 | 9/2006 | Blann et al. | 585/511 |
| 2006/0229480 A1 | 10/2006 | Blann et al. | 585/535 |
| 2009/0062493 A1 * | 3/2009 | De Boer et al. | 526/145 |

FOREIGN PATENT DOCUMENTS

| | | | |
|---|---|---|---|
| WO | WO0204119 | | 1/2002 |
| WO | WO2004/056478 | * | 7/2004 |
| WO | WO 2004056479 | | 7/2004 |
| WO | WO2005039758 | | 5/2005 |
| WO | WO 2005/123884 | * | 12/2005 |

OTHER PUBLICATIONS

Anthea Carter, Steven A. Cohen, Neil A. Cooley, Aden Murphy, James Scott, and Duncan F. Wass, "High Activity Ethylene Trimerisation Catalysts Based on Diphosphine Ligands," The Royal Society of Chemistry 2002, CHEMCOMM 2002, pp. 858-859.

* cited by examiner

*Primary Examiner*—Melvin C Mayes
*Assistant Examiner*—Yun Qian

(57) ABSTRACT

A catalyst precursor composition comprising: a source of chromium, molybdenum or tungsten; a first ligand having the general formula $(R^1)(R^2P—X—P(R^3)(R^4)$; and a second ligand having the general formula $(R^{1'})(R^{2'})P—X'—P(R^{3'})(R^{4'})$. The present invention also relates to a catalyst system comprising the catalyst precursor composition of the present invention and a cocatalyst. The present invention further relates to a process for the trimerization and tetramerization of olefinic monomers, particularly the trimerization and tetramerization of ethylene to 1-hexene and 1-octene, wherein the process comprises contacting at least one olefinic monomer with the catalyst system of the present invention.

14 Claims, No Drawings

CATALYTIC OLIGOMERIZATION OF OLEFINIC MONOMERS

FIELD OF THE INVENTION

The present invention relates to a catalyst system for the oligomerization of olefinic monomers. The present invention also relates to a process for the oligomerization of olefinic monomers.

BACKGROUND OF THE INVENTION

The efficient catalytic trimerization or tetramerization of olefinic monomers, such as the trimerization and tetramerization of ethylene to 1-hexene and 1-octene, is an area of great interest for the production of olefinic trimers and tetramers of varying degrees of commercial value. In particular, 1-hexene is a valuable comonomer for linear low-density polyethylene (LLDPE) and 1-octene is valuable as a chemical intermediate in the production of plasticizer alcohols, fatty acids, detergent alcohol and lubrication oil additives as well as a valuable comonomer in the production of polymers such as polyethylene. 1-Hexene and 1-octene can be produced by a conventional transition metal oligomerization process, although the trimerization and tetramerization routes are preferred.

Several different catalytic systems have been disclosed in the art for the trimerization of ethylene to 1-hexene. A number of these catalysts are based on chromium.

U.S. Pat. No. 6,800,702 (BP) discloses a catalyst for the trimerization of olefins comprising a source of chromium, molybdenum or tungsten, a ligand containing at least one phosphorus, arsenic or antimony atom bound to at least one hydrocarbyl or heterohydrocarbyl group having a polar substituent, but excluding the case where all such polar substituents are phosphane, arsane or stibane groups, and optionally an activator. The ligand used in most of the examples is (2-methoxyphenyl)$_2$PN(Me)P(2-methoxyphenyl)$_2$.

Although the catalysts disclosed in the BP documents mentioned above have good selectivity for 1-hexene within the $C_6$ fraction, a relatively high level of by-product formation (e.g. $C_{10}$ by-products) is typically observed.

Catalytic systems for the tetramerization of ethylene to 1-octene have recently been described. A number of these catalysts are based on chromium.

U.S. 2006/0173226 and U.S. 2006/0229480 (Sasol) disclose catalyst compositions and processes for the tetramerization of olefins. The catalyst compositions disclosed in U.S. 2006/0173226 comprise a transition metal and a heteroatomic ligand having the general formula (R)$_n$A-B—C(R)$_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group of which at least one R group is substituted with a polar substituent and n and m are determined by the respective valence and oxidation state of A and/or C. The catalyst compositions disclosed in U.S. 2006/0229480 comprise a transition metal and a heteroatomic ligand having the general formula (R')$_n$A-B—C(R')$_m$ where A, B, C, n and m are as defined above, and R' is independently selected from any homo or heterohydrocarbyl group.

U.S. 2006/0128910 (Sasol) discloses the tandem tetramerization and polymerisation of ethylene. Specifically, U.S. 2006/0128910 discloses a process for polymerising olefins to produce branched polyolefins in the presence of a distinct polymerization catalyst and a distinct tetramerization catalyst, wherein the tetramerization catalyst produces 1-octene in a selectivity greater than 30% and the 1-octene produced is at least partially incorporated into the polyolefin chain.

Although the tetramerization catalysts disclosed in the Sasol documents mentioned above have good selectivity for 1-octene within the $C_8$ fraction, again, a relatively high level of by-product formation is observed. Typically, the by-product consists of $C_6$ compositions; however, only about 70 to 80% wt. of the $C_6$ by-product composition is 1-hexene, with the remaining $C_6$ by-product comprising compounds such as methylcyclopentane and methylenecyclopentane. The presence of these remaining $C_6$ by-product compositions, which have very little commercial use or value, is highly undesirable from both an economic point of view as well as from a product separation point of view.

It has now been surprisingly found that the catalyst system and process of the present invention provide an efficient route for the selective production of 1-hexene and 1-octene from ethylene while reducing the level of by-product formation, especially $C_{10}$ by-products, solids (i.e. heavy waxes and/or polyethylene) and $C_6$ compositions/isomers other than 1-hexene.

SUMMARY OF THE INVENTION

The present invention relates to a catalyst precursor composition comprising:
  a) a source of chromium, molybdenum or tungsten;
  b) a first ligand having the general formula (I);

$$(R^1)(R^2)P—X—P(R^3)(R^4) \quad (I)$$

wherein:
X is a bridging group of the formula —N($R^5$)—, wherein $R^5$ is selected from hydrogen, a hydrocarbyl group, a substituted hydrocarbyl group, a heterohydrocarbyl group, a substituted heterohydrocarbyl group, a silyl group or derivative thereof;
at least three of $R^1$ to $R^4$ are independently selected from optionally substituted aromatic groups, each bearing a polar substituent on at least one of the ortho-positions; and
optionally one of $R^1$ to $R^4$ is independently selected from hydrocarbyl, substituted hydrocarbyl, heterohydrocarbyl and substituted heterohydrocarbyl groups with the proviso that when the group is aromatic it does not contain a polar substituent at any of the ortho-positions;
  c) a second ligand having the general formula (II);

$$(R^{1'})(R^{2'})P—X'—P(R^{3'})(R^{4'}) \quad (II)$$

wherein:
X' is a bridging group as defined for X of the first ligand, component (b), of general formula (I);
at least $R^{1'}$ and $R^{2'}$ of $R^{1'}$ to $R^{4'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions; and optionally none, one or both of $R^{3'}$ and $R^{4'}$ are independently selected from an optionally substituted aromatic group bearing a polar substituent on at least one of the ortho-positions.

In another embodiment, the present invention also relates to a catalyst system comprising the catalyst precursor composition of the present invention and an additional component;
  d) a cocatalyst.

The present invention also relates to a process for the trimerization and tetramerization of olefinic monomers, particularly the trimerization and tetramerization of ethylene to 1-hexene and 1-octene, wherein the process comprises contacting at least one olefinic monomer with the catalyst system of the present invention under trimerization and tetramerization reaction conditions.

The present invention further relates to the use of the catalyst system of the present invention for the trimerization and tetramerization of olefinic monomers, especially for the trimerization and tetramerization of ethylene to 1-hexene and 1-octene.

DETAILED DESCRIPTION OF THE INVENTION

As used herein, the term "trimerization" means the catalytic trimerization of an olefinic monomer to give a product composition enriched in the compound derived from the reaction of three of said olefinic monomers. The term trimerization includes the cases wherein all the olefinic monomers in the feed stream are identical as well as the cases wherein the feed stream contains two or more different olefinic monomers.

In particular, the term "trimerization" when used in relation to the trimerization of ethylene means the trimerization of ethylene to form a $C_6$ alkene, especially 1-hexene.

The term "trimerization selectivity" when used in relation to the trimerization of ethylene means the amount of $C_6$ fraction formed within the product composition.

The term "1-hexene selectivity" when used in relation to the trimerization of ethylene means the amount of 1-hexene formed within the $C_6$ fraction of the product composition. The overall yield of 1-hexene in the trimerization of ethylene is the product of the "trimerization selectivity" multiplied by the "1-hexene selectivity".

The term "tetramerization" means the catalytic tetramerization of an olefinic monomer to give a product composition enriched in the compound derived from the reaction of four of said olefinic monomers. The term tetramerization includes the cases wherein all the olefinic monomers in the feed stream are identical as well as the cases wherein the feed stream contains two or more different olefinic monomers.

In particularly, the term "tetramerization" when used in relation to the tetramerization of ethylene means the tetramerization of ethylene to form a $C_8$ alkene, especially 1-octene.

The term "tetramerization selectivity" when used in relation to the tetramerization of ethylene means the amount of $C_8$ fraction formed within the product composition.

The term "1-octene selectivity" when used in relation to the tetramerization of ethylene means the amount of 1-octene formed within the $C_8$ fraction of the product composition. The overall yield of 1-octene in the tetramerization of ethylene is the product of the "tetramerization selectivity" multiplied by the "1-octene selectivity".

In one embodiment of the present invention, the catalyst precursor composition comprises the following components:
 a) a source of chromium, molybdenum or tungsten;
 b) the first ligand; and
 c) the second ligand;

In another embodiment of the present invention, the catalyst system comprises the following components:
 a) a source of chromium, molybdenum or tungsten;
 b) the first ligand;
 c) the second ligand; and
 d) a cocatalyst.

Each of these four catalyst components is described in detail below.

The source of chromium, molybdenum or tungsten, component (a), for the catalyst system can include simple inorganic and organic salts of chromium, molybdenum or tungsten. Examples of simple inorganic and organic salts are halides, acetylacetonates, carboxylates, oxides, nitrates, sulfates and the like. Further sources of chromium, molybdenum or tungsten can also include co-ordination and organometallic complexes, for example chromium trichloride tris-tetrahydrofuran complex, (benzene)tricarbonylchromium, chromium hexacarbonyl, and the like. Preferably, the source of chromium, molybdenum or tungsten, component (a), for the catalyst system is selected from simple inorganic and organic salt of chromium, molybdenum or tungsten.

In one embodiment of the present invention, the source of chromium, molybdenum or tungsten, component (a), for the catalyst system is a simple inorganic or organic salt of chromium, molybdenum or tungsten, which is soluble in a solvent such as those mentioned in U.S. Pat. No. 6,800,702 which is herein incorporated by reference in its entirety.

The source of chromium, molybdenum or tungsten can also include a mixture of any combination of simple inorganic salts, simple organic salts, co-ordination complexes and organometallic complexes.

In a preferred embodiment herein, component (a) is a source of chromium, particularly chromium (III).

Preferred sources of chromium for use herein are simple inorganic and organic salts of chromium and co-ordination or organometallic complexes of chromium. More preferred sources of chromium for use herein are the simple inorganic and organic salts of chromium, such as salts of carboxylic acids, preferably salts of alkanoic acids containing 1 to 30 carbon atoms, salts of aliphatic-β-diketones and salts of β-ketoesters (e.g. chromium (III) 2-ethylhexanoate, chromium (III) octanoate and chromium (III) acetylacetonate), and halide salts of chromium, such as chromium trichloride, chromium trichloride tris-tetrahydrofuran complex, chromium tribromide, chromium trifluoride, and chromium tri-iodide. Specific examples of preferred sources of chromium for use herein are chromium (III) acetylacetonate, also called chromium tris(2,4-pentanedionate), $Cr(acac)_3$, chromium trichloride, $CrCl_3$, and chromium trichloride tris-tetrahydrofuran complex, $CrCl_3(THF)_3$.

The first ligand of the catalyst precursor composition and/or catalyst system of the present invention, component (b), is of the general formula (I);

(R$^1$)(R$^2$)P—X—P(R$^3$)(R$^4$)     (I)

wherein X and $R^1$ to $R^4$ are defined above.

The bridging group X is of the formula —N($R^5$)—, wherein $R^5$ is preferably a hydrocarbyl group, a substituted hydrocarbyl group, a heterohydrocarbyl group, a substituted heterohydrocarbyl group, a silyl group or derivative thereof. Typically, $R^5$ is selected from hydrogen or the groups consisting of alkyl, substituted alkyl, aryl, substituted aryl, aryloxy, substituted aryloxy, alkenyl, substituted alkenyl, cycloalkyl, substituted cycloalkyl, alkoxycarbonyl, carbonyloxy, alkoxy, aminocarbonyl, carbonylamino, dialkylamino, silyl groups or derivatives thereof, and alkyl or aryl groups substituted with any of these substituents or halogen or a nitro group. More preferably $R^5$ is an alkyl, substituted alkyl (including heterocyclic substituted alkyl with at least one heteroatom, such as N or O, and alkyl groups substituted with a heteroatom or heteroatomic group), cycloalkyl, substituted cycloalkyl, substituted cyclic aryl, substituted aryl, aryloxy or substituted aryloxy group. Examples of suitable $R^5$ groups include $C_1$-$C_{15}$ alkyl groups, substituted $C_1$-$C_{15}$ alkyl groups, $C_2$-$C_{15}$ alkenyl groups, substituted $C_2$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups. Most preferred $R^5$ groups are the $C_1$-$C_{15}$ alkyl groups, especially $C_1$-$C_6$ alkyl groups, which include both linear and branched alkyl groups; suitable examples include methyl, ethyl, propyl, isopropyl, butyl, isobutyl, t-butyl, pentyl, alkyl branched pentyl groups, hexyl, alkyl branched hexyl groups, heptyl, alkyl branched heptyl groups, octyl and alkyl branched octyl groups.

Examples of suitable bridging groups include —N(methyl)-, —N(ethyl)-, —N(propyl)-, —N(isopropyl)-, —N(butyl)-, —N(t-butyl)-, —N(pentyl)-, —N(hexyl)-, —N(2-ethylhexyl)-, —N(cyclohexyl)-, —N(1-cyclohexylethyl)-, —N(2-methylcyclohexyl)-, —N(benzyl)-, —N(phenyl)-, —N(2-octyl)-, —N(p-methoxyphenyl)-, —N(p-t-butylphenyl)-, —N(($CH_2$)$_3$—N-morpholine)-, —N(Si($CH_3$)$_3$)—, —N($CH_2CH_2CH_2$Si(OMe)$_3$))—, —N(decyl)- and —N(allyl)-.

The term "hydrocarbyl" as used herein refers to a group only containing carbon and hydrogen atoms. The hydrocarbyl group may be a saturated or unsaturated, linear or branched alkyl, a non-aromatic ring or an aromatic ring. Unless otherwise stated, the preferred hydrocarbyl groups for use herein are those containing from 1 to 20 carbon atoms.

The term "substituted hydrocarbyl" as used herein refers to hydrocarbyl groups which contain one or more inert heteroatom containing functional groups. By "inert heteroatom containing functional groups" is meant that the functional groups do not interfere to any substantial degree with the trimerization and tetramerization process.

The term "heterohydrocarbyl" as used herein refers to a hydrocarbyl group wherein one or more of the carbon atoms is replaced by a heteroatom, such as S, N or O. The carbon atom of the hydrocarbyl group which is replaced by a heteroatom can be either an internal carbon atom of the hydrocarbyl group or the carbon atom through which the heterohydrocarbyl group is attached, e.g. the atom which is attached to the nitrogen atom in the case of the bridging group, e.g. —N(OMe)—. The term "substituted heterohydrocarbyl" as used herein refers to heterohydrocarbyl groups which contain one or more inert heteroatom containing functional groups.

The term "aromatic" as used herein, refers to a monocyclic or polycyclic, aromatic or heteroaromatic ring having from 5 to 14 ring atoms, optionally containing from 1 to 3 heteroatoms selected from N, O and S. Preferably, the aromatic groups are monocyclic or polycyclic aromatic rings, such as cyclopentadienyl (which can also include ferrocenyl groups), phenyl, naphthyl or anthracenyl. Unless otherwise stated, the preferred aromatic groups are monocyclic or polycyclic aromatic rings having from 5 to 10 ring atoms, more preferred aromatic groups are monocyclic aromatic rings containing from 5 to 6 carbon atoms, such as phenyl and cyclopentadienyl, and a most preferred aromatic group is a phenyl group. The term "substituted aromatic" as used herein means that the aromatic group may be substituted with one or more substituents.

By the term "ortho-position" when used in relation to substituents on aromatic $R^1$ to $R^4$ groups, it is meant that the substituent is in the ortho position relative to the atom bonded to the phosphorus atom.

The substituents on the $R^1$ to $R^4$ groups can contain carbon atoms and/or heteroatoms. The substituents may be either polar or non-polar. Suitable substituents include hydrocarbyl groups which may be straight-chain or branched, saturated or unsaturated, aromatic or non-aromatic. The hydrocarbyl substituents may optionally contain heteroatoms such as Si, S, N or O. Suitable aromatic hydrocarbyl substituents include monocyclic and polycyclic aromatic groups, preferably having from 5 to 10 carbon atoms in the ring, such as phenyl and $C_1$-$C_4$ alkyl phenyl groups. Suitable non-aromatic hydrocarbyl substituents include linear or branched alkyl or cycloalkyl groups, preferably having from 1 to 10 carbon atoms, more preferably 1 to 4 carbon atoms.

Other suitable substituents on the $R^1$ to $R^4$ groups include halides such as chloride, bromide and iodide, thiol, —OH, $A^1$-O—, —S-$A^1$, —CO-$A^1$, —$NH_2$, —$NHA^1$, —$NA^1A^2$, —CO—$NA^1A^2$, —$NO_2$, =O, in which $A^1$ and $A^2$, independently, are non-aromatic groups preferably having from 1 to 10 carbon atoms, more preferably 1 to 4 carbon atoms, e.g. methyl, ethyl, propyl and isopropyl.

When the $R^1$ to $R^4$ groups of the first ligand are substituted, preferred substituents are hydrocarbyl groups. Particularly preferred hydrocarbyl substituents are $C_1$-$C_4$ alkyl groups, preferably methyl, ethyl, propyl, isopropyl, butyl, isobutyl, most preferably methyl.

In one embodiment of the first ligand, three $R^1$ to $R^4$ groups are independently selected from optionally substituted aromatic groups, each bearing a polar substituent on at least one of the ortho-positions, and one $R^1$ to $R^4$ group is independently selected from hydrocarbyl, substituted hydrocarbyl, heterohydrocarbyl and substituted heterohydrocarbyl groups with the proviso that when the group is aromatic it does not contain a polar substituent at any of the ortho-positions. In another embodiment of the first ligand, all four $R^1$ to $R^4$ groups are independently selected from optionally substituted aromatic groups, each bearing a polar substituent on at least one of the ortho-positions.

At least three of the $R^1$ to $R^4$ groups of the first ligand are independently selected from optionally substituted aromatic groups, each bearing a polar substituent on at least one of the ortho-positions. In an embodiment, at least three of $R^1$ to $R^4$ are o-anisyl. For the avoidance of doubt, the phrase "bearing a polar substituent on at least one of the ortho-positions" means that, in the same ligand, the $R^1$ to $R^4$ group which bears the polar substituent is substituted with a polar substituent on one or both of its ortho positions.

The term "optionally substituted" in relation to the $R^1$ to $R^4$ groups of the first ligand which are independently selected from optionally substituted aromatic groups, each bearing a polar substituent on at least one of the ortho-positions, means that, in addition to the polar substituent on at least one of the ortho-positions, the $R^1$ to $R^4$ group may contain one or more other substituents.

Polar is defined by IUPAC as an entity with a permanent electric dipole moment. Therefore, as used herein, the term "polar substituents" means a substituent which incorporates a permanent electric dipole moment.

Suitable polar substituents for use herein include but are not necessarily limited to, optionally branched $C_1$-$C_{20}$ alkoxy groups, i.e. $R^1$ to $R^4$ substituted with a hydrocarbyl group connected through an oxygen bridging atom; optionally substituted $C_5$-$C_{14}$ aryloxy groups, i.e. $R^1$ to $R^4$ substituted with an optionally substituted aromatic group connected through an oxygen bridging atom; optionally branched $C_1$-$C_{20}$ alkoxy($C_1$-$C_{20}$)alkyl groups, i.e. $R^1$ to $R^4$ substituted with a $C_1$-$C_{20}$ hydrocarbyl group bearing a $C_1$-$C_{20}$ alkoxy group; hydroxyl; amino; (di-)$C_1$-$C_6$ alkylamino; nitro; $C_1$-$C_6$ alkylsulphonyl; $C_1$-$C_6$ alkylthio($C_1$-$C_6$)alkyl groups; sulphate; heterocyclic groups, especially with at least one N and/or O ring atom; and tosyl groups.

Examples of suitable polar substituents include methoxy, ethoxy, isopropoxy, phenoxy, pentafluorophenoxy, trimethylsiloxy, dimethylamino, methylsulphonyl, tosyl, methoxymethyl, methylthiomethyl, 1,3-oxazolyl, hydroxyl, amino, methoxymethyl, phosphino, arsino, stibino, sulphate, nitro and the like.

Preferably, the polar substituents in the $R^1$ to $R^4$ groups independently selected from optionally substituted aromatic groups, each bearing a polar substituent on at least one of the ortho-positions, are independently selected from optionally branched $C_1$-$C_{20}$ alkoxy groups, optionally substituted $C_5$-$C_{14}$ aryloxy groups, and optionally branched $C_1$-$C_{20}$ alkyl ($C_1$-$C_{20}$)alkoxy groups. More preferably, the polar substituents are independently selected from optionally branched $C_1$-$C_{20}$ alkoxy groups, especially optionally branched $C_1$-$C_6$ alkoxy groups such as, for example, methoxy, ethoxy or isopropoxy of which methoxy is a particularly preferred polar substituent; alternatively, longer optionally branched $C_1$-$C_{20}$ alkoxy groups such as optionally branched $C_8$-$C_{20}$ alkoxy groups, for example decyloxy, dodecyloxy, tetradecyloxy, hexadecyloxy, octadecyloxy or eicosanoxy groups, of which eicosanoxy is preferred, may be preferred as the polar substituents in order to increase the solubility of the ligand in organic media.

It is preferred that the $R^1$ to $R^4$ groups of the first ligand which are independently selected from optionally substituted aromatic groups, each bearing a polar substituent on at least one of the ortho-positions, are the same and bear the same number and type of polar substituent(s). It is particularly preferred that each of said $R^1$ to $R^4$ groups bears a polar substituent on only one of their two ortho-positions, for example o-anisyl.

In a first embodiment of the first ligand wherein one of $R^1$ to $R^4$ is independently selected from hydrocarbyl, substituted hydrocarbyl, heterohydrocarbyl and substituted heterohydrocarbyl groups with the proviso that when the group is aromatic it does not contain a polar substituent at any of the ortho-positions, it is preferred that each of said $R^1$ to $R^4$ group is independently selected from substituted or unsubstituted aromatic groups, including substituted or unsubstituted heteroaromatic groups, which do not contain a polar substituent at any of the ortho-positions.

In one aspect of said first embodiment, said $R^1$ to $R^4$ group may be independently selected from a group comprising optionally substituted benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl and tetrahydrofuranyl groups. In another embodiment of the first ligand, said $R^1$ to $R^4$ group may be independently selected from a group comprising optionally substituted phenyl, tolyl, biphenyl, naphthyl, thiophenyl and ethyl groups.

In a second aspect of said first embodiment, said $R^1$ to $R^4$ group is independently selected from optionally substituted phenyl groups which do not contain a polar substituent at any of the ortho-positions, or alternatively, do not contain any polar substituents at all. Any polar substituent present in said $R^1$ to $R^4$ groups may be electron donating. Said $R^1$ to $R^4$ groups may optionally contain non-polar substituent.

IUPAC defines non-polar as an entity without a permanent electric dipole moment.

Suitable non-polar substituents may be a methyl, ethyl, propyl, butyl, isopropyl, isobutyl, tert-butyl, pentyl, hexyl, cyclopentyl, 2-methylcyclohexyl, cyclohexyl, cylopentadienyl, phenyl, bi-phenyl, naphthyl, tolyl, xylyl, mesityl, ethenyl, propenyl and benzyl group, or the like. Preferably, the non-polar substituent is not electron donating.

In one specific aspect of said first embodiment, said $R^1$ to $R^4$ group is an unsubstituted phenyl group.

Optionally, any of the groups $R^1$ to $R^4$ may independently be linked to one or more of each other or to the bridging group X to form a cyclic structure.

The ligands according to formula (I) can be prepared using procedures known to one skilled in the art or disclosed in published literature. Examples of such compounds include: (2-methoxyphenyl)(phenyl)PN(methyl)P(2-methoxyphenyl)$_2$, (2-methoxyphenyl)$_2$PN(methyl)P(2-methoxyphenyl)$_2$, (2-methoxyphenyl)(phenyl)PN(ethyl)P(2-methoxyphenyl)$_2$, (2-methoxyphenyl)$_2$PN(ethyl)P(2-methoxyphenyl)$_2$, (2-ethoxyphenyl)(phenyl)PN(methyl)P(2-methoxyphenyl)$_2$, (2-ethoxyphenyl)$_2$PN(methyl)P(2-methoxyphenyl)$_2$, (2-ethoxyphenyl)(phenyl)PN(methyl)P(2-ethoxyphenyl)$_2$, (2-ethoxyphenyl)$_2$PN(methyl)P(2-ethoxyphenyl)$_2$, (2-ethoxyphenyl)(phenyl)PN(ethyl)P(2-methoxyphenyl)$_2$, (2-ethoxyphenyl)$_2$PN(ethyl)P(2-methoxyphenyl)$_2$, (2-ethoxyphenyl)(phenyl)PN(ethyl)P(2-ethoxyphenyl)$_2$, (2-ethoxyphenyl)$_2$PN(ethyl)P(2-ethoxyphenyl)$_2$, (2-methoxyphenyl)$_2$PN(methyl)P(2-isopropoxyphenyl)$_2$, (2-methoxyphenyl)(phenyl)PN(methyl)P(2-methoxyphenyl)$_2$, (2-methoxyphenyl)$_2$PN(methyl)P(2-methoxyphenyl)$_2$, (2-methoxyphenyl)(phenyl)PN(ethyl)P(2-isopropoxyphenyl)$_2$, (2-methoxyphenyl)$_2$PN(ethyl)P(2-isopropoxyphenyl)$_2$, (2-methoxyphenyl)(phenyl)PN(ethyl)P(2-methoxyphenyl)$_2$, (2-methoxyphenyl)$_2$PN(ethyl)P(2-methoxyphenyl)$_2$, (2-ethoxyphenyl)(phenyl)PN(methyl)P(2-isopropoxyphenyl)$_2$, (2-ethoxyphenyl)$_2$PN(methyl)P(2-isopropoxyphenyl)$_2$, (2-ethoxyphenyl)(phenyl)PN(methyl)P(2-ethoxyphenyl)$_2$, (2-ethoxyphenyl)$_2$PN(methyl)P(2-ethoxyphenyl)$_2$, (2-ethoxyphenyl)(phenyl)PN(ethyl)P(2-isopropoxyphenyl)$_2$, (2-ethoxyphenyl)$_2$PN(ethyl)P(2-isopropoxyphenyl)$_2$, (2-ethoxyphenyl)(phenyl)PN(ethyl)P(2-ethoxyphenyl)$_2$, (2-ethoxyphenyl)$_2$PN(ethyl)P(2-ethoxyphenyl)$_2$, (2-isopropoxyphenyl)(phenyl)PN(methyl)P(2-isopropoxyphenyl)$_2$, (2-isopropoxyphenyl)$_2$PN(methyl)P(2-isopropoxyphenyl)$_2$, (2-isopropoxyphenyl)(phenyl)PN(ethyl)P(2-isopropoxyphenyl)$_2$, (2-isopropoxyphenyl)$_2$PN(ethyl)P(2-isopropoxyphenyl)$_2$, (2-methoxyphenyl)(phenyl)PN(methyl)P(2-isopropoxyphenyl)$_2$, (2-methoxyphenyl)(phenyl)PN(propyl)P(2-methoxyphenyl)$_2$, (2-methoxyphenyl)$_2$PN(propyl)P(2-methoxyphenyl)$_2$, (2-methoxyphenyl)(phenyl)PN(isopropyl)P(2-methoxyphenyl)$_2$, (2-methoxyphenyl)$_2$PN(isopropyl)P(2-methoxyphenyl)$_2$, (2-ethoxyphenyl)(phenyl)PN(propyl)P(2-methoxyphenyl)$_2$, (2-ethoxyphenyl)$_2$PN(propyl)P(2-methoxyphenyl)$_2$, (2-ethoxyphenyl)(phenyl)PN(propyl)P(2-ethoxyphenyl)$_2$, (2-ethoxyphenyl)$_2$PN(propyl)P(2-ethoxyphenyl)$_2$, (2-ethoxyphenyl)(phenyl)PN(isopropyl)P(2-methoxyphenyl)$_2$, (2-ethoxyphenyl)$_2$PN(isopropyl)P(2-methoxyphenyl)$_2$, (2-ethoxyphenyl)(phenyl)PN(isopropyl)P(2-ethoxyphenyl)$_2$, (2-ethoxyphenyl)$_2$PN(isopropyl)P(2-ethoxyphenyl)$_2$, (2-methoxyphenyl)$_2$PN(propyl)P(2-isopropoxyphenyl)$_2$, (2-methoxyphenyl)(phenyl)PN(propyl)P(2-methoxyphenyl)$_2$, (2-methoxyphenyl)$_2$PN(propyl)P(2-methoxyphenyl)$_2$, (2-methoxyphenyl)(phenyl)PN(isopropyl)P(2-isopropoxyphenyl)$_2$, (2-methoxyphenyl)$_2$PN(isopropyl)P(2-isopropoxyphenyl)$_2$, (2-methoxyphenyl)(phenyl)PN(isopropyl)P(2-methoxyphenyl)$_2$, (2-methoxyphenyl)$_2$PN(isopropyl)P(2-methoxyphenyl)$_2$, (2-ethoxyphenyl)(phenyl)PN(propyl)P(2-isopropoxyphenyl)$_2$, (2-ethoxyphenyl)$_2$PN(propyl)P(2-isopropoxyphenyl)$_2$, (2-ethoxyphenyl)(phenyl)PN(propyl)P(2-ethoxyphenyl)$_2$, (2-ethoxyphenyl)$_2$PN(propyl)P(2-ethoxyphenyl)$_2$, (2-ethoxyphenyl)(phenyl)PN(isopropyl)P(2-isopropoxyphenyl)$_2$, (2-ethoxyphenyl)$_2$PN(isopropyl)P(2-isopropoxyphenyl)$_2$, (2-ethoxyphenyl)(phenyl)PN(isopropyl)P(2-ethoxyphenyl)$_2$, (2-ethoxyphenyl)$_2$PN(isopropyl)P(2- ethoxyphenyl)₂, (2-isopropoxyphenyl)(phenyl)PN(propyl)P(2-isopropoxyphenyl)₂, (2-isopropoxyphenyl)₂PN(propyl)P(2-isopropoxyphenyl)₂, (2-isopropoxyphenyl)(phenyl)PN(isopropyl)P(2-isopropoxyphenyl)₂, (2-isopropoxyphenyl)₂PN(isopropyl)P(2-isopropoxyphenyl)₂, (2-methoxyphenyl)(phenyl)PN(propyl)P(2-isopropoxyphenyl)₂, (2-methoxyphenyl)(phenyl)PN(butyl)P(2-methoxyphenyl)₂, (2-methoxyphenyl)₂PN(butyl)P(2-methoxyphenyl)₂, (2-methoxyphenyl)(phenyl)PN(t-butyl)P(2-methoxyphenyl)₂, (2-methoxyphenyl)₂PN(t-butyl)P(2-methoxyphenyl)₂, (2-ethoxyphenyl)(phenyl)PN(butyl)P(2-methoxyphenyl)₂, (2-ethoxyphenyl)₂PN(butyl)P(2-methoxyphenyl)₂, (2-ethoxyphenyl)(phenyl)PN(butyl)P(2-ethoxyphenyl)₂, (2-ethoxyphenyl)₂PN(butyl)P(2-ethoxyphenyl)₂, (2-ethoxyphenyl)(phenyl)PN(t-butyl)P(2-methoxyphenyl)₂, (2-ethoxyphenyl)₂PN(t-butyl)P(2-methoxyphenyl)₂, (2-ethoxyphenyl)(phenyl)PN(t-butyl)P(2-ethoxyphenyl)₂, (2-ethoxyphenyl)₂PN(t-butyl)P(2-ethoxyphenyl)₂, (2-methoxyphenyl)₂PN(butyl)P(2-isopropoxyphenyl)₂, (2-methoxyphenyl)(phenyl)PN(butyl)P(2-methoxyphenyl)₂, (2-methoxyphenyl)₂PN(butyl)P(2-methoxyphenyl)₂, (2-methoxyphenyl)(phenyl)PN(t-butyl)P(2-isopropoxyphenyl)₂, (2-methoxyphenyl)₂PN(t-butyl)P(2-isopropoxyphenyl)₂, (2-methoxyphenyl)(phenyl)PN(t-butyl)P(2-methoxyphenyl)₂, (2-methoxyphenyl)₂PN(t-butyl)P(2-methoxyphenyl)₂, (2-ethoxyphenyl)(phenyl)PN(butyl)P(2-isopropoxyphenyl)₂, (2-ethoxyphenyl)₂PN(butyl)P(2-isopropoxyphenyl)₂, (2-ethoxyphenyl)(phenyl)PN(butyl)P(2-ethoxyphenyl)₂, (2-ethoxyphenyl)₂PN(butyl)P(2-ethoxyphenyl)₂, (2-ethoxyphenyl)(phenyl)PN(t-butyl)P(2-isopropoxyphenyl)₂, (2-ethoxyphenyl)₂PN(t-butyl)P(2-isopropoxyphenyl)₂, (2-ethoxyphenyl)(phenyl)PN(t-butyl)P(2-ethoxyphenyl)₂, (2-ethoxyphenyl)₂PN(t-butyl)P(2-ethoxyphenyl)₂, (2-isopropoxyphenyl)(phenyl)PN(butyl)P(2-isopropoxyphenyl)₂, (2-isopropoxyphenyl)₂PN(butyl)P(2-isopropoxyphenyl)₂, (2-isopropoxyphenyl)(phenyl)PN(t-butyl)P(2-isopropoxyphenyl)₂, (2-isopropoxyphenyl)₂PN(t-butyl)P(2-isopropoxyphenyl)₂, (2-methoxyphenyl)(phenyl)PN(butyl)P(2-isopropoxyphenyl)₂, (2-methoxyphenyl)(phenyl)PN(phenyl)P(2-methoxyphenyl)₂, (2-methoxyphenyl)₂PN(phenyl)P(2-methoxyphenyl)₂, (2-methoxyphenyl)(phenyl)PN(cyclohexyl)P(2-methoxyphenyl)₂, (2-methoxyphenyl)₂PN(cyclohexyl)P(2-methoxyphenyl)₂, (2-ethoxyphenyl)(phenyl)PN(phenyl)P(2-methoxyphenyl)₂, (2-ethoxyphenyl)₂PN(phenyl)P(2-methoxyphenyl)₂, (2-ethoxyphenyl)(phenyl)PN(phenyl)P(2-ethoxyphenyl)₂, (2-ethoxyphenyl)₂PN(phenyl)P(2-ethoxyphenyl)₂, (2-ethoxyphenyl)(phenyl)PN(cyclohexyl)P(2-methoxyphenyl)₂, (2-ethoxyphenyl)₂PN(cyclohexyl)P(2-methoxyphenyl)₂, (2-ethoxyphenyl)(phenyl)PN(cyclohexyl)P(2-ethoxyphenyl)₂, (2-ethoxyphenyl)₂PN(cyclohexyl)P(2-ethoxyphenyl)₂, (2-methoxyphenyl)₂PN(phenyl)P(2-isopropoxyphenyl)₂, (2-methoxyphenyl)(phenyl)PN(phenyl)P(2-methoxyphenyl)₂, (2-methoxyphenyl)₂PN(phenyl)P(2-methoxyphenyl)₂, (2-methoxyphenyl)(phenyl)PN(cyclohexyl)P(2-isopropoxyphenyl)₂, (2-methoxyphenyl)₂PN(cyclohexyl)P(2-isopropoxyphenyl)₂, (2-methoxyphenyl)(phenyl)PN(cyclohexyl)P(2-methoxyphenyl)₂, (2-methoxyphenyl)₂PN(cyclohexyl)P(2-methoxyphenyl)₂, (2-ethoxyphenyl)(phenyl)PN(phenyl)P(2-isopropoxyphenyl)₂, (2-ethoxyphenyl)₂PN(phenyl)P(2-isopropoxyphenyl)₂, (2-ethoxyphenyl)(phenyl)PN(phenyl)P(2-ethoxyphenyl)₂, (2-ethoxyphenyl)₂PN(phenyl)P(2-ethoxyphenyl)₂, (2-ethoxyphenyl)(phenyl)PN(cyclohexyl)P(2-isopropoxyphenyl)₂, (2-ethoxyphenyl)₂PN(cyclohexyl)P(2-isopropoxyphenyl)₂, (2-ethoxyphenyl)(phenyl)PN(cyclohexyl)P(2-ethoxyphenyl)₂, (2-ethoxyphenyl)₂PN(cyclohexyl)P(2-ethoxyphenyl)₂, (2-isopropoxyphenyl)(phenyl)PN(phenyl)P(2-isopropoxyphenyl)₂, (2-isopropoxyphenyl)₂PN(phenyl)P(2-isopropoxyphenyl)₂, (2-isopropoxyphenyl)(phenyl)PN(cyclohexyl)P(2-isopropoxyphenyl)₂, (2-isopropoxyphenyl)₂PN(cyclohexyl)P(2-isopropoxyphenyl)₂, (2-methoxyphenyl)(phenyl)PN(phenyl)P(2-isopropoxyphenyl)₂, (2-eicosanoxyphenyl)(phenyl)PN(methyl)P(2-eicosanoxyphenyl)₂, (2-eicosanoxyphenyl)₂PN(methyl)P(2-eicosanoxyphenyl)₂, (2-methoxyphenyl)(2-eicosanoxyphenyl)PN(methyl)P(2-eicosanoxyphenyl)₂, (2-methoxyphenyl)₂PN(methyl)P(2-eicosanoxyphenyl)₂, (2-ethoxyphenyl)(2-eicosanoxyphenyl)PN(isopropyl)P(2-eicosanoxyphenyl)₂, and the like.

The second ligand of the catalyst precursor composition and/or catalyst system of the present invention, component (c), is of the general formula (II);

$$(R^{1'})(R^{2'})P-X'-P(R^{3'})(R^{4'}) \quad (II)$$

wherein X' and $R^{1'}$ to $R^{4'}$ are as defined above.

In a first embodiment of the second ligand, the $R^{1'}$ and $R^{2'}$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions, and the $R^{3'}$ and $R^{4'}$ groups are independently selected from an optionally substituted aromatic group bearing a polar substituent on at least one of the ortho-positions. In another embodiment of the second ligand, the $R^{1'}$, $R^{2'}$ and at least one of $R^{3'}$ and $R^{4'}$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions, and one of the $R^{3'}$ or $R^{4'}$ groups is independently selected from an optionally substituted aromatic group bearing a polar substituent on at least one of the ortho-positions. In another embodiment of the second ligand, all four $R^{1'}$ to $R^{4'}$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions.

In the embodiment of the second ligand which comprises one or two of the $R^{3'}$ or $R^{4'}$ groups which are independently selected from an optionally substituted aromatic group bearing a polar substituent on at least one of the ortho-positions, said $R^{3'}$ or $R^{4'}$ group is as defined for the at least three $R^1$ to $R^4$ groups which are independently selected from optionally substituted aromatic groups, each bearing a polar substituent on at least one of the ortho-positions, in the first ligand, component (b), of general formula (I).

The at least $R^{1'}$ and $R^{2'}$ of $R^{1'}$ to $R^{4'}$ groups of the second ligand which are independently selected from hydrocarbyl, substituted hydrocarbyl, heterohydrocarbyl and substituted heterohydrocarbyl groups with the proviso that when the group is aromatic it does not contain a polar substituent at any of the ortho-positions are as defined for the optional one $R^1$ to $R^4$ group which is independently selected from hydrocarbyl, substituted hydrocarbyl, heterohydrocarbyl and substituted heterohydrocarbyl groups with the proviso that when the group is aromatic it does not contain a polar substituent at any of the ortho-positions, in the first ligand, component (b), of general formula (I).

In one embodiment of the second ligand wherein the $R^{1'}$ to $R^{4'}$ are independently selected from hydrocarbyl, substituted hydrocarbyl, heterohydrocarbyl and substituted heterohydrocarbyl groups with the proviso that when the groups are aromatic they do not contain a polar substituent at any of the ortho-positions, said $R^{1'}$ to $R^{4'}$ are aromatic, including heteroaromatic, but only none, one, two or three of said $R^{1'}$ to $R^{4'}$ groups may be substituted by any substituent on an atom adjacent to the atom bound to the phosphorus atom; preferably not more than two of said $R^{1'}$ to $R^{4'}$ groups may have substituents on the atom adjacent to the atom bound to the phosphorus atom.

In another embodiment of the present invention, one or both of the phosphorus atoms of the second ligand may be independently oxidised by S, Se, N or O. Typically, neither of the phosphorus atoms of the second ligand is oxidised by S, Se, N or O.

The second ligand may also optionally contain multiple $(R^{1'})(R^{2'})P$—X—$P(R^{3'})(R^{4'})$ units. Non limiting examples of such ligands include ligands where the individual units are coupled either via one or more of the $R^{1'}$, $R^{2'}$, $R^{3'}$ or $R^{4'}$ groups or via the bridging group X. Typically, the second ligand does not contain multiple $(R^{1'})(R^{2'})P$—X—$P(R^{3'})(R^{4'})$ units.

The ligands can be prepared using procedures known to one skilled in the art and procedures disclosed in published literature.

Examples of the second ligands of general formula (II) according to the present invention include: (3-methoxyphenyl)$_2$PN(methyl)P(3-methoxyphenyl)$_2$, (4-methoxyphenyl)$_2$PN(methyl)P(4-methoxyphenyl)$_2$, (3-methoxyphenyl)$_2$PN(isopropyl)P(3-methoxyphenyl)$_2$, (4-methoxyphenyl)$_2$PN(isopropyl)P(4-methoxyphenyl)$_2$, (4-methoxyphenyl)$_2$PN(2-ethylhexyl)P(4-methoxyphenyl)$_2$, (3-methoxyphenyl)(phenyl)PN(methyl)P(phenyl)$_2$, (4-methoxyphenyl)(phenyl)PN(methyl)P(phenyl)$_2$, (3-methoxyphenyl)(phenyl)PN(methyl)P(3-methoxyphenyl)(phenyl), (4-methoxyphenyl)(phenyl)PN(methyl)P(4-methoxyphenyl)(phenyl), (3-methoxyphenyl)$_2$PN(methyl)P(phenyl)$_2$, (4-methoxyphenyl)$_2$PN(methyl)P(phenyl)$_2$, (4-methoxyphenyl)$_2$PN(1-cyclohexylethyl)P(4-methoxyphenyl)$_2$, (4-methoxyphenyl)$_2$PN(2-methylcyclohexyl)P(4-methoxyphenyl)$_2$, (4-methoxyphenyl)$_2$PN(decyl)P(4-methoxyphenyl)$_2$, (4-methoxyphenyl)$_2$PN(pentyl)P(4-methoxyphenyl)$_2$, (4-methoxyphenyl)$_2$PN(benzyl)P(4-methoxyphenyl)$_2$, (4-methoxyphenyl)$_2$PN(phenyl)P(4-methoxyphenyl)$_2$, (2-methoxyphenyl)(phenyl)PN(methyl)P(phenyl)$_2$, (2-methoxyphenyl)(phenyl)PN(methyl)P(phenyl)$_2$, (4-fluorophenyl)$_2$PN(methyl)P(4-fluorophenyl)$_2$, (4-dimethylamino-phenyl)$_2$PN(methyl)P(4-dimethylamino-phenyl)$_2$, (4-methoxyphenyl)$_2$PN(allyl)P(4-methoxyphenyl)$_2$, (phenyl)$_2$PN(isopropyl)P(2-methoxyphenyl)$_2$, (4-(4-methoxyphenyl)-phenyl)$_2$PN(isopropyl)P(4-(4-methoxyphenyl)phenyl)$_2$, (4-methoxyphenyl)(phenyl)PN(isopropyl)P(phenyl)$_2$, 1,2-di-(N(P(4-methoxyphenyl)$_2$)$_2$)-benzene, 1,4-di-(N(P(4-methoxyphenyl)$_2$)$_2$)-benzene, N(CH$_2$CH$_2$N(P(4-methoxyphenyl)$_2$)$_2$)$_3$ and 1,4-di-(P(4-methoxyphenyl)N(methyl)P(4-methoxyphenyl)$_2$)-benzene. (phenyl)$_2$PN(methyl)P(phenyl)$_2$, (phenyl)$_2$PN(pentyl)P(phenyl)$_2$, (phenyl)$_2$PN(phenyl)P(phenyl)$_2$, (phenyl)$_2$PN(p-methoxyphenyl)P(phenyl)$_2$, (phenyl)$_2$PN(p-t-butylphenyl)P(phenyl)$_2$, (phenyl)$_2$PN((CH$_2$)$_3$—N-morpholine)P(phenyl)$_2$, (phenyl)$_2$PN(Si(CH$_3$)$_3$)P(phenyl)$_2$, (ethyl)$_2$PN(methyl)P(ethyl)$_2$, (ethyl)$_2$PN(isopropyl)P(phenyl)$_2$, (ethyl)(phenyl)P-N(methyl)P(ethyl)(phenyl), (ethyl)(phenyl)PN(isopropyl)P(phenyl)$_2$, (phenyl)$_2$P(=Se)N(isopropyl)P(phenyl)$_2$, (o-ethylphenyl)(phenyl)PN(isopropyl)P(phenyl)$_2$, (o-methylphenyl)$_2$PN(isopropyl)P(o-methylphenyl)(phenyl), (phenyl)$_2$PN(benzyl)P(phenyl)$_2$, (phenyl)$_2$PN(1-cyclohexylethyl)P(phenyl)$_2$, (phenyl)$_2$PN[CH$_2$CH$_2$CH$_2$Si(OMe$_3$)]P(phenyl)$_2$, (phenyl)$_2$PN(cyclohexyl)P(phenyl)$_2$, (phenyl)$_2$PN(2-methylcyclohexyl)P(phenyl)$_2$, (phenyl)$_2$PN(allyl)P(phenyl)$_2$, (2-naphthyl)$_2$PN(methyl)P(2-naphthyl)$_2$, (p-biphenyl)$_2$PN(methyl)P(p-biphenyl)$_2$, (p-methylphenyl)$_2$PN(methyl)P(p-methylphenyl)$_2$, (2-thiophenyl)$_2$PN(methyl)P(2-thiophenyl)$_2$, (m-methylphenyl)$_2$PN(methyl)P(m-methylphenyl)$_2$, (phenyl)$_2$PN(isopropyl)P(phenyl)$_2$, (phenyl)$_2$P(=S)N(isopropyl)P(phenyl)$_2$, 1,2-di-(N(P(phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P(phenyl)$_2$)-benzene, (3-eicosanoxyphenyl)$_2$PN(methyl)P(3-eicosanoxyphenyl)$_2$, (4-eicosanoxyphenyl)$_2$PN(methyl)P(4-eicosanoxyphenyl)$_2$, (3-eicosanoxyphenyl)(phenyl)PN(methyl)P(phenyl)$_2$, (3-eicosanoxyphenyl)$_2$PN(methyl)P(phenyl)$_2$, (3-eicosanoxyphenyl)(phenyl)PN(methyl)P(3-eicosanoxyphenyl)(phenyl), (4-eicosanoxyphenyl)(phenyl)PN(methyl)P(4-eicosanoxyphenyl)(phenyl), (4-eicosanoxyphenyl)$_2$PN(methyl)P(4-eicosanoxyphenyl)(phenyl), and the like.

In one specific embodiment of the present invention the catalyst precursor composition comprises:

a) a source of chromium, molybdenum or tungsten;
b) a first ligand having the general formula (I);

$$(R^1)(R^2)P—X—P(R^3)(R^4) \quad (I)$$

wherein:

X is a bridging group of the formula —N(R$^5$)—, wherein R$^5$ is selected from hydrogen, a hydrocarbyl group, a substituted hydrocarbyl group, a heterohydrocarbyl group, a substituted heterohydrocarbyl group, a silyl group or derivative thereof;

all four of $R^1$ to $R^4$ are independently selected from optionally substituted aromatic groups, each bearing a polar substituent on at least one of the ortho-positions; and c) a second ligand having the general formula (II);

$$(R^{1'})(R^{2'})P—X'—P(R^{3'})(R^{4'}) \quad (II)$$

wherein:

X' is a bridging group as defined for X of the first ligand, component (b), of general formula (I);

$R^{1'}$ and $R^{2'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions; and $R^{3'}$ and $R^{4'}$ are independently selected from an optionally substituted aromatic group bearing a polar substituent on at least one of the ortho-positions.

In another specific embodiment of the present invention the catalyst composition comprises:

a) a source of chromium, molybdenum or tungsten;
b) a first ligand having the general formula (I);

$$(R^1)(R^2)P—X—P(R^3)(R^4) \quad (I)$$

wherein:

X is a bridging group of the formula —N(R$^5$)—, wherein R$^5$ is selected from hydrogen, a hydrocarbyl group, a substituted hydrocarbyl group, a heterohydrocarbyl group, a substituted heterohydrocarbyl group, a silyl group or derivative thereof;

all four of $R^1$ to $R^4$ are independently selected from optionally substituted aromatic groups, each bearing a polar substituent on at least one of the ortho-positions; and c) a second ligand having the general formula (II);

$$(R^{1'})(R^{2'})P—X'—P(R^{3'})(R^{4'}) \quad (II)$$

wherein:

X' is a bridging group as defined for X of the first ligand, component (b), of general formula (I);

$R^{1'}$ and $R^{2'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions; and R$^{3'}$ and R$^{4'}$ are independently selected from an optionally substituted aromatic group bearing a polar substituent on at least one of the ortho-positions; and d) a cocatalyst.

In another specific embodiment of the present invention the catalyst precursor composition comprises:

a) a source of chromium, molybdenum or tungsten;
b) a first ligand of the general formula (I);

$$(R^1)(R^2)P—X—P(R^3)(R^4) \qquad (I)$$

wherein:

X is a bridging group of the formula —N(R$^5$)—, wherein R$^5$ is selected from hydrogen, a hydrocarbyl group, a substituted hydrocarbyl group, a heterohydrocarbyl group, a substituted heterohydrocarbyl group, a silyl group or derivative thereof; and all four of R$^1$ to R$^4$ are independently selected from optionally substituted aromatic groups, each bearing a polar substituent on at least one of the ortho-positions; and c) a second ligand of the general formula (II);

$$(R^{1'})(R^{2'})P—X'—P(R^{3'})(R^{4'}) \qquad (II)$$

wherein:

X' is a bridging group as defined for X in the first ligand of general formula (I); and all four of R$^{1'}$ to R$^{4'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

In another specific embodiment of the present invention, the catalyst system comprises:

a) a source of chromium, molybdenum or tungsten;
b) a first ligand of the general formula (I);

$$(R^1)(R^2)P—X—P(R^3)(R^4) \qquad (I)$$

wherein:

X is a bridging group of the formula —N(R$^5$)—, wherein R$^5$ is selected from hydrogen, a hydrocarbyl group, a substituted hydrocarbyl group, a heterohydrocarbyl group, a substituted heterohydrocarbyl group, a silyl group or derivative thereof; and all four of R$^1$ to R$^4$ are independently selected from optionally substituted aromatic groups, each bearing a polar substituent on at least one of the ortho-positions;

c) a second ligand of the general formula (II);

$$(R^{1'})(R^{2'})P—X'—P(R^{3'})(R^{4'}) \qquad (II)$$

wherein:

X' is a bridging group as defined for X in the first ligand of general formula (I); and all four of R$^{1'}$ to R$^{4'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions; and d) a cocatalyst.

The catalyst precursor composition and catalyst system of the present invention may independently comprise more than one first ligand as defined above and more than one second ligand as defined above.

The first ligand and the second ligand can be present in the catalyst system in a molar ratio in the range of from 100:1 to 1:100. In a preferred embodiment the molar ratio of the first ligand to the second ligand is in the range of from about 10:1 to about 1:10, more preferably in the range of from about 5:1 to about 1:5.

By varying the ratio of the first ligand and the second ligand in the catalyst precursor composition or the catalyst system of the present invention, the ratio of trimers and tetramers produced in the process of the present invention can be varied. As a general principle, by increasing the amount of the first ligand relative to the second ligand in the catalyst system, the concentration of trimers in the reaction product composition increases relative to the concentration of the tetramers in the reaction product composition, and vice-versa.

Therefore, the catalyst system of the present invention can be used in a tuneable process for the trimerization and tetramerization of olefinic monomers. By the term "tuneable" as used herein, it is meant that by varying the amounts of the components of the present invention, the amount of trimers and tetramers in the product composition produced by the process of the present invention may be varied. This may be useful for a tuneable, continuous or semi-continuous, process for the trimerization and tetramerization of olefinic monomers, wherein the product composition can be changed (e.g. from producing a higher proportion of trimers to a higher proportion of tetramers, or vice-versa,) by changing the ratio of the first and second ligand that are fed into the reactor without having to interrupt the olefinic monomer feed or the trimerization and tetramerization product flow. In particular, this may be especially useful for a tuneable, continuous or semi-continuous, process for the trimerization and tetramerization of ethylene, wherein the product composition can be changed (e.g. from producing a higher proportion of 1-hexene to a higher proportion of 1-octene, or vice-versa) by changing the ratio of the first and second ligand that are fed into the reactor without having to interrupt the olefinic monomer feed or the trimerization and tetramerization product flow.

The amount of chromium, molybdenum or tungsten, namely component (a), and the total amount of the ligand components, i.e. the combined amount of the first and second ligands, namely components (b) and (c), can be present in the catalyst precursor composition or the catalyst system of the present invention in a molar ratio in the range from 10000:1 to 1:10000, preferably from 100:1 to 1:100, more preferably from 10:1 to 1:10 (moles of component (a):moles of component (b)+(c)). Most preferably, the chromium, molybdenum or tungsten, component (a), and the combined amounts of the ligand components, components (b) and (c), are present in a molar ratio in the range from 3:1 to 1:3. Generally the molar ratio of the amount of component (a) and the combined amount of components (b) and (c) are present in a molar ratio in the range from 1.5:1 to 1:3, especially approximately equal or one halve.

The cocatalyst, component (d), may in principle be any compound or mixture of compounds that generates an active catalyst system with the source of chromium, molybdenum or tungsten, component (a), and the first and second ligands, components (b) and (c) (i.e. the catalyst precursor composition).

Compounds which are suitable for use as a cocatalyst include organoaluminium compounds, organoboron compounds, organic salts, such as methyllithium and methylmagnesium bromide and inorganic acids and salts, such as tetrafluoroboric acid etherate, silver tetrafluoroborate, sodium hexafluoroantimonate and the like.

Particularly preferred cocatalysts are organoaluminium compounds. Suitable organoaluminium compounds for use herein are those having the formula AlR$^6_3$, wherein each R$^6$ group is independently selected from C$_1$-C$_{30}$ alkyl (preferably C$_1$-C$_{12}$ alkyl), oxygen containing moieties or halides, and compounds such as LiAlH$_4$ and the like. Non-limiting examples of suitable organoaluminium compounds include trimethylaluminium (TMA), triethylaluminium (TEA), tri-n-butyl aluminium, triisobutylaluminium (TIBA), tri-n-octyla-luminium, methylaluminium dichloride, ethylaluminium dichloride, dimethylaluminium chloride, diethylaluminium chloride and aluminoxanes (also called alumoxanes). Mixtures of organoaluminium compounds are also suitable for use herein.

In a preferred embodiment herein, the cocatalyst is an aluminoxane cocatalyst. These aluminoxane cocatalysts may comprise any aluminoxane compound or a mixture of aluminoxane compounds. Aluminoxanes may be prepared by the controlled addition of water to an alkylaluminium compound, such as those mentioned above, or are available commercially. Non-limiting examples of suitable aluminoxanes include methyl aluminoxane (MAO), modified methyl aluminoxane (MMAO), tetraisobutyl dialuminoxane (TIBAO), tetra-n-butyl dialuminoxane and tetra-n-octyl dialuminoxane. In this context it should be noted that the term "aluminoxane" as used within this specification includes commercially available aluminoxanes, which are derived from the corresponding trialkylaluminium by addition of water and which may contain from 2 to 15% wt., typically about 5% wt., but optionally about 10% wt., of aluminum.

Other suitable co-catalysts include those mentioned in U.S. Pat. No. 6,800,702, U.S. 2006/0173226 and U.S. 2006/0229480, the disclosures of which are incorporated herein in their entirety by reference.

The quantity of cocatalyst in the catalyst system the present invention is typically enough to provide a ratio in the range from 0.1 to 20,000, preferably from 1 to 2000, more preferably 1 to 1000, most preferably 1 to 500, aluminum or boron atoms per atom of chromium, molybdenum or tungsten.

The three catalyst components of the catalyst precursor composition, (a), (b) and (c), and the fourth component of the catalyst system, (d), may be added together simultaneously or sequentially in any order so as to provide an active catalyst. The three catalyst components of the catalyst precursor composition, (a), (b) and (c), and the fourth component of the catalyst system, (d), may be contacted in the presence of any suitable solvent. Suitable solvents are known to those skilled in the art, suitable solvents may include any inert solvent that does not react with the co-catalyst component, such as saturated aliphatic, unsaturated aliphatic, aromatic, halogenated hydrocarbons and ionic liquids. Typical solvents include, but are not limited to, benzene, toluene, xylene, ethylbenzene, cumene, propane, butane, pentane, heptane, decane, dodecane, tetradecane, methylcyclohexane, methylcycopentane, cyclohexane, 1-hexene, 1-octene and the like. Other examples of suitable solvents are those disclosed in WO 02/04119, such as hydrocarbon solvents and polar solvents such as diethyl ether, tetrahydrofuran, acetonitrile, and the like.

In one embodiment of the present invention, the catalyst system is formed by adding the co-catalyst component, (d), to a catalyst precursor composition of the present invention.

The catalyst system of the present invention may be prepared either in the presence (i.e. "in-situ") or absence of the olefinic monomer. The three catalyst components of the catalyst precursor composition, (a), (b) and (c) and the fourth component of the catalyst system, (d), may be combined fully in the absence of the olefinic monomer, or the olefinic monomer may be included prior to contacting the components of the catalyst system, simultaneously with the components of the catalyst system or at any point in the process of contacting the components of the catalyst.

Another method for forming the catalyst system of the present invention includes combining a first solution of components (a) and (b), and optionally component (d), with a second solution of components (a) and (c), and optionally component (d), wherein additional amounts of components (a), (b), (c) and (d) may be further added to the combined solution, if necessary, to form the desired catalyst system. The combining of the above mentioned first and second solutions and any additional components may be performed either in-situ or in the absence of the olefinic monomer.

The three catalyst components of the catalyst precursor composition, (a), (b) and (c), and the fourth component of the catalyst system, (d), may be combined at a temperature in the range of from −100 to 200° C., preferably 0 to 150° C., more preferably 20 to 100° C.

The catalyst system of the present invention may be unsupported or supported on a support material. Examples of suitable support materials can be found in U.S. Pat. No. 6,800,702, U.S. 2006/0173226 and U.S. 2006/0229480.

The olefinic monomers suitable for use in the trimerization and tetramerization process of the present invention can be any olefinic monomers, which can be converted into a trimer or tetramer. Suitable olefinic monomers include, but are not necessarily limited to, ethylene, propylene, optionally branched $C_4$-$C_{24}$, preferably $C_4$-$C_{20}$, α-olefins, optionally branched $C_4$-$C_{24}$, preferably $C_4$-$C_{20}$, internal olefins, optionally branched $C_4$-$C_{24}$, preferably C4-$C_{20}$, vinylidene olefins, optionally branched $C_4$-$C_{24}$, preferably C4-$C_{20}$, cyclic olefins and optionally branched $C_4$-$C_{24}$, preferably C4-$C_{20}$, dienes, as well as optionally branched $C_4$-$C_{24}$, preferably C4-$C_{20}$, functionalized olefins. Examples of suitable olefinic monomers include, but are not necessarily limited to, linear α-olefins, such as ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene and 1-eicosene; branched α-olefins such as 4-methylpent-1-ene and 1-ethyl-1-hexene; linear and branched internal-olefins such as 2-butene; styrene; cyclohexene; norbornene and the like.

Mixtures of olefinic monomers can also be used in the process of the present invention.

Preferred olefinic monomers for use in the trimerization and tetramerization process of the present invention are propylene and ethylene. Especially preferred is ethylene.

The catalyst system and process of the present invention are particularly useful for the simultaneous trimerization and tetramerization of ethylene to 1-hexene and 1-octene.

The trimerization and tetramerization process of the present invention can be performed under a range of process conditions known to one skilled in the art of trimerization and tetramerization or disclosed in published literature such as, for example, those disclosed in U.S. Pat. No. 6,800,702, U.S. 2006/0173226 and U.S. 2006/0229480.

The simultaneous trimerization and tetramerization reaction can be performed in solution phase, slurry phase, gas phase or bulk phase.

When the simultaneous trimerization and tetramerization is performed in solution or slurry phase, a diluent or solvent, which is substantially inert under trimerization and tetramerization conditions may be employed. Suitable diluents or solvents are aliphatic and aromatic hydrocarbons, halogenated hydrocarbons and olefins which are substantially inert under trimerization and tetramerization conditions may be employed, such as those disclosed in U.S. Pat. No. 6,800,702, U.S. 2006/0173226 and U.S. 2006/0229480.

The trimerization and tetramerization process of the present invention may be performed in any one of a number of suitable reactors, which are well known to one skilled in the art. Typically the trimerization and tetramerization process of the present invention is carried out in a batch, semi-batch or continuous mode.

The trimerization and tetramerization process of the present invention may be carried out under a wide range of reaction conditions, which are well known to a person skilled in the art of trimerization and tetramerization. Typically, the temperature will be in the range from −100° C. to 200° C., preferably from 0° C. to 150° C., and more preferably from 20° C. to 100° C. The pressure range under which the process of the present invention may be performed is not critical and may vary depending upon the limitations of the reactor, typically the reaction pressure will be in the range of from below atmospheric pressure to about 500 barg. Preferably, the pressure will be in the range from 0 to 100 barg, more preferably from 1 to 50 barg.

In one embodiment of the present invention, there is a process for the trimerization and tetramerization of olefinic monomers, wherein the process comprises contacting at least one olefinic monomer under trimerization and tetramerization reaction conditions with a catalyst system of the present invention, wherein the process is a continuous or semi-continuous process and the ratio of the catalyst components, especially the ratio of the first ligand and the second ligand, is varied during the process. Variation of the ratio of the first ligand and the second ligand can be performed to make continual adjustments to a process to ensure a consistent product composition or can be performed to a process to change the product composition produced. A preferred version of this embodiment is a process for the trimerization and tetramerization of ethylene, wherein the process comprises contacting ethylene under trimerization and tetramerization reaction conditions with a catalyst system of the present invention, wherein the process is a continuous or semi-continuous process and the ratio of the catalyst components, especially the first ligand and the second ligand, is varied during the process.

Separation of the products, reactant and catalyst can be performed by any technique known to one skilled in the art, such as distillation, filtration, centrifugation, liquid/liquid separation, extraction, etc.

Further details regarding suitable reaction conditions, including further details on reactors, solvents, separation techniques, and the like, can be found in U.S. Pat. No. 6,800,702.

The use of the catalyst system and process of the present invention for the catalytic trimerization and tetramerization of olefinic monomers provides a simplified method of producing trimers and tetramers of the olefinic monomer with reduced formation of by-products compared with the combination of the product compositions of separate trimerization and tetramerization processes. In particular, the use of the catalyst system and process of the present invention for the catalytic trimerization and tetramerization of ethylene to 1-hexene and 1-octene provides a process with very high selectivity for 1-hexene and 1-octene over all the other products formed in the reaction.

The overall yield of 1-hexene and 1-octene in the process of the present invention depends upon the ratio of the first ligand, component (b), and the second ligand, component (c).

The trimerization and tetramerization selectivity (i.e. the amount of trimers and tetramers of the olefinic monomers in the overall product composition) of the process of the present invention is at least 70% wt, preferably at least 80% wt, more preferably at least 90% wt, of the overall product composition. The trimerization and tetramerization selectivity for the trimerization and tetramerization of ethylene (i.e. the amount of $C_6$ and $C_8$ fraction in the overall product composition) using the catalyst system of the present invention is at least 87% wt, preferably at least 88% wt, more preferably at least 90% wt, of the overall product composition.

The amount of 1-hexene produced by the trimerization and tetramerization of ethylene using the catalyst system of the present invention is typically in the range of from 10% wt to 90% wt, preferably from 15% wt to 85% wt, more preferably from 20% wt to 80% wt, of the overall product composition. The amount of 1-octene produced by the trimerization and tetramerization of ethylene using the catalyst system of the present invention is typically in the range of from 10% wt to 90% wt, preferably from 15% wt to 85% wt, more preferably from 20% wt to 80% wt, of the overall product composition. In one aspect of the invention, amount of 1-octene produced by the trimerization and tetramerization of ethylene using the catalyst system of the present invention is in the range of from 10% wt to 30% wt.

The 1-hexene selectivity (i.e. the amount of 1-hexene present in the $C_6$ fraction of the product composition) in the trimerization and tetramerization of ethylene using the catalyst system of the present invention is preferably at least 80% wt, more preferably at least 85% wt, even more preferably at least 90% wt and most preferably at least 95% wt, of the $C_6$ fraction of the product composition.

The 1-octene selectivity (i.e. the amount of 1-octene present in the $C_8$ fraction of the product composition) in the trimerization and tetramerization of ethylene using the catalyst system of the present invention is preferably at least 80% wt, more preferably at least 85% wt, even more preferably at least 90% wt and most preferably at least 95% wt, $C_8$ fraction of the product composition.

In practice, the combined 1-hexene and the 1-octene yield is typically at least 88% wt of the overall product composition.

In another embodiment of the present invention, the olefinic product composition of the trimerization and tetramerization of ethylene using the catalyst system of the present invention typically comprises a combined total content of 1-hexene and 1-octene in the range of from 88 to 98% wt of the overall product composition, preferably from 90 to 98% wt and more preferably from 92 to 98% wt, wherein the 1-hexene content is at least 10% wt, more preferably at least 15% wt and most preferably at least 20% wt, of the overall product composition and the 1-octene content is at least 10% wt, more preferably at least 15% wt and most preferably at least 20% wt, of the overall product composition.

In further embodiment of the present invention, the olefinic product composition of the trimerization and tetramerization of ethylene using the catalyst system of the present invention comprises a total content of compounds other than 1-hexene and 1-octene of at most 12% wt of the overall product composition, preferably at most 10% wt and more preferably at most 8% wt, wherein the 1-hexene content is at least 10% wt, more preferably at least 15% wt and most preferably at least 20% wt, of the overall product composition and the 1-octene content is at least 10% wt, more preferably at least 15% wt and most preferably at least 20% wt, of the overall product composition. Typically, the olefinic product composition of the trimerization and tetramerization of ethylene using the catalyst system of the present invention comprises a total content of compounds other than 1-hexene and 1-octene in the range of from 2 to 12% wt of the overall product composition, preferably from 2 to 10% wt and more preferably from 2 to 8% wt, wherein the 1-hexene content is at least 10% wt of the overall product composition and the 1-octene content is at least 10% wt of the overall product composition. Typically, the product composition also comprises at most 2.0% wt of $C_6$ compounds other than 1-hexene, at most 1.0% wt of $C_8$ compounds other than 1-octene, at most 5.0% wt of $C_{10}$ compounds and at most 2.0% wt of hydrocarbon compounds comprising 12 or more carbon atoms. The catalyst systems and process of the present invention are illustrated by the following non-limiting examples.

EXAMPLES

General Procedures and Characterisation

All chemicals used in preparations were purchased from Aldrich and used without further purification unless mentioned otherwise.

All the operations with the catalyst systems were carried out under nitrogen atmosphere. All solvents used were dried using standard procedures. Anhydrous toluene (99.8% purity) was dried over 4 Å molecular sieves (final water content of about 3 ppm). Anhydrous heptane (99.8% purity) was dried by passage over 4 Å molecular sieves (final water content of about 1 ppm).

Ethylene (99.5% purity) was purified over a column containing 4 Å molecular sieves and BTS catalyst (BASF) in order to reduce water and oxygen content to <1 ppm.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. The yields of the $C_4$-$C_{30}$ olefins were obtained from the GC analysis.

The "trimerization selectivity", "tetramerization selectivity", "1-hexene selectivity" and "1-octene selectivity" were all determined by GC analysis.

The amount of "solids", mainly consisting of heavy wax and polyethylene, has been determined by weighing, after its isolation from the reactor wall and appendages, followed by washing with toluene on a glass filter (P3) and by vacuum drying.

The amount of "total product" is the sum of the amount of largely olefinic product derived from GC analysis and the amount of solids.

The NMR data was obtained at room temperature with a Varian 300 MHz or 400 MHz apparatus.

Catalyst Systems

The catalyst systems of the present invention were prepared from catalyst precursor compositions containing ligands A, B, C, and D either individually or in any combination, and a chromium source, these components are described below.

Chromium Source

Chromium trichloride tris(tetrahydrofuran) complex, i.e. $CrCl_3(THF)_3$, and chromium tris(2,4-pentanedionate), also called chromium tris(acetylacetonate), i.e. $Cr(acac)_3$, have been used as the chromium sources in the simultaneous tri- and tetramerisation reactions of ethylene.

Ligand A (Comparative)

The (2-methoxyphenyl)(phenyl)PN(CH₃)P(2-methoxyphenyl)(phenyl) ligand was prepared by first forming a suspension of 0.42 g lithium (60 mmol) in 80 ml of tetrahydrofuran (THF), to which was added 9.66 g of (2-methoxyphenyl)₂P(phenyl) (30 mmol) at 0° C. under an argon atmosphere. The mixture was stirred for 4 hours, after which time a 5 ml aliquot of methanol was added. 60 ml of toluene was added to the mixture, after which the solution was extracted with two 40 ml portions of water. The extracted toluene solution was then concentrated to a volume of approximately 20 ml, which resulted in formation of a suspension. The concentrated toluene solution was filtered, and 4.6 g of $C_2Cl_6$ was added to the toluene filtrate, which was then stirred for 2 hours at 90° C. The HCl gas, which evolved from the reaction, was "trapped" in an alkali bath. The mixture was then cooled to room temperature and purged with nitrogen to remove all of the remaining HCl present in the solution.

At room temperature, a 5 ml aliquot of triethylamine was added to the concentrated toluene solution and left for a few minutes, after which 6 ml of 2 M H₂NMe (12 mmol) was added a few drops at a time. The suspension was filtered and washed with 20 ml of toluene. The toluene filtrate and the toluene wash fraction were combined. The combined toluene fractions were evaporated to dryness and 30 ml of methanol was added. The methanol solution was left overnight at −35° C. wherein a white (2-methoxyphenyl)(phenyl)PN(CH₃)P(2-methoxyphenyl)(phenyl) precipitate was formed in the solution. The precipitated ligand was then isolated.

The precipitated ligand consisted of two isomers, a racemic isomer (the RR and/or the SS enantiomers of the ligand) and a meso isomer (the RS enantiomer of the ligand). The proportions of these two isomers were determined by $^{31}P$ NMR with peaks at 63.18 and 64.8 ppm corresponding to the two different isomers respectively. One sample of (2-methoxyphenyl)(phenyl)PN(CH₃)P(2-methoxyphenyl)(phenyl) was used in the examples. This sample consisted of a mixture of both the racemic and the meso isomers having weight ratios of 92/8, designated as A.

Composition A'

(2-methoxyphenyl)(phenyl)PN(CH₃)P(2-methoxyphenyl)(phenyl) in a 1:1 molar ratio with $CrCl_3(THF)_3$ was prepared by stirring an equimolar mixture of $CrCl_3(THF)_3$ and ligand component A in toluene for 1 hour at 50° C., followed by evaporation of the solvent in vacuum and washing of the residue with pentane.

Ligand B (First Ligand)

The (2-methoxyphenyl)₂PN(CH₃)P(2-methoxyphenyl)₂ ligand was prepared by first forming a solution of 1.59 g (5 mmol) (2-methoxyphenyl)₂PNEt₂ in 20 ml diethyl ether. To this solution 10 ml of a 1 M HCl solution in diethyl ether (10 mmol HCl) was added under an inert atmosphere at room temperature. The suspension thus formed was stirred overnight. The diethyl ether was removed from the product under vacuum and 20 ml of dry toluene was added. The resulting solution was filtered and the toluene was removed from the filtrate under vacuum to yield a white solid (2-methoxyphenyl)₂PCl product.

A solution of 0.51 g (5 mmol) of triethylamine in 20 ml of dry dichloromethane was added to the (2-methoxyphenyl)₂PCl product. To the resulting mixture, 1.25 ml of a 2 M H₂NMe solution in THF (2.5 mmol) was added and allowed to stir overnight. The solvents were removed from the resulting solution in vacuo and 20 ml of dry toluene was added. The mixture was then filtered. The toluene was removed from the filtrate under vacuum, and 10 ml of methanol was added to the residue to produce a suspension, which was filtered once more, to leave the solid white (2-methoxyphenyl)₂PN(CH₃)P(2-methoxyphenyl)₂ product which was isolated.

Composition B'

(2-methoxyphenyl)$_2$PN(CH$_3$)P(2-methoxyphenyl)$_2$ in a 1:1 molar ratio with CrCl$_3$(THF)$_3$ was prepared similarly to Composition A'.

Ligand C (Second Ligand)

The (phenyl)$_2$PN(isopropyl)P(phenyl)$_2$ ligand was prepared by the following method. At 0° C., under a nitrogen atmosphere, 15 ml triethylamine was added to 6.3 g (phenyl)$_2$PCl in 80 ml of dry dichloromethane. To the resulting mixture, 0.844 g isopropylamine was added and allowed to stir overnight at room temperature. The solvents were removed from the resulting solution in-vacuo and 50 ml of dry toluene was added. The mixture was then filtered over a small layer of silica. The toluene was removed from the filtrate under vacuum, (phenyl)$_2$PN(isopropyl)P(phenyl)$_2$ product was isolated as a white solid. Crystallization from ethanol yielded (phenyl)$_2$PN(isopropyl)P(phenyl)$_2$ as white crystals.

Ligand D (Second Ligand)

The (phenyl)$_2$PN(isopropyl)P(2-methoxyphenyl)$_2$ ligand was prepared by the following method. Under a nitrogen atmosphere, 12 ml triethylamine was added to 3.39 g isopropylamine in 10 ml dry toluene. To the resulting mixture, 5.15 ml (phenyl)$_2$PCl was slowly added and allowed to stir overnight at room temperature. The precipitate was removed by filtration. The solvents were removed from the resulting solution in vacuo. To the evaporation residue, pentane was added. The solvent was then removed in vacuo from the pentane solution, yielding (phenyl)$_2$PNH(isopropyl) as a colourless oil, which crystallized on standing at room temperature.

Under a nitrogen atmosphere, 3 ml triethyl amine was added to 0.9 g of the isolated (phenyl)$_2$PNH(isopropyl) in 5 ml of dry dichloromethane. To the resulting mixture, 1.1 g of (2-methoxyphenyl)$_2$PCl was added and allowed to stir for a week at room temperature. To the resulting reaction mixture, 5-10 ml of dry toluene was added. The precipitate was removed by centrifugation. The solvents were removed from the resulting solution in vacuo. The resulting mixture was first washed with pentane and then methanol was added to the solution under stirring to yield a white solid. The white solid was washed with pentane and dried in vacuo. Yield –0.7 g of (phenyl)$_2$PN(isopropyl)P(2-methoxyphenyl)$_2$.

Co-Catalyst

The co-catalyst used in the experiments below was selected from:

modified methyl aluminoxane (MMAO) wherein about 25% of the methyl groups are replaced with isobutyl groups. MMAO-3A in heptane ([Al]=6.42% wt), available from AKZO-NOBEL Chemicals B. V., Amersfoort, The Netherlands;

methyl aluminoxane (MAO) in toluene, [Al]=5.20% wt, supplied by Crompton GmbH, Bergkamen, Germany.

Examples 1-11

Catalyst System Preparation for Simultaneous Trimerization and Tetramerization in a Batch Autoclave In a Braun MB 200-G dry box the CrCl$_3$ 1:1 complexes of ligand A or B (i.e. Compositions A' or B', indicated in Table 1) and the relative amount of ligand component C or D if present, indicated in Table 1, were placed in a glass bottle. The catalyst precursor composition was converted into the catalyst solution by adding 3 mmol of MAO solution in toluene (1.6 g MAO solution), followed by typically 4 g of dry toluene, finally the bottle was sealed by a septum cap.

Alternatively, chromium tris(acetylacetonate) and the relative amount of ligand components A, B, C, and D, as indicated in Table 1, were placed in a glass bottle, to which dry toluene (typically 4 g) was added to obtain the catalyst precursor solution. Finally the bottle was sealed with a septum cap.

These catalyst solutions or catalyst precursor solutions (the chromium tris(acetylacetonate) solutions are introduced as catalyst precursor solution which is to be activated by the pre-dosed MAO or MMAO in-situ in the autoclave), or part of these solutions, were used in the simultaneous tri- and tetramerization reaction of ethylene.

Simultaneous Trimerization and Tetramerization Reactions of Ethylene in a 1.0-Litre Batch Autoclave Simultaneous tri- and tetramerization experiments were performed in a 1.0-litre steel autoclave equipped with jacket cooling with a heating/cooling bath (ex. Julabo, model ATS-2) and a turbine/gas stirrer and baffles.

The reactor was scavenged by introducing 250 ml toluene, MAO (0.6 g solution) and subsequent stirring at 70° C. under nitrogen pressure of 0.4-0.5 MPa for 30 min. The reactor contents were discharged via a tap in the base of the autoclave. The reactor was evacuated to about 0.4 kPa and loaded with approximately 250 ml toluene or heptane, heated to 40° C. and pressurized with ethylene to 15 barg.

Whilst stirring, a MAO-solution was added to the reactor with the aid of toluene to obtain an overall Al/Cr atomic ratio of 200:1 (the total volume solution injected was about 25 ml: the MAO-solution diluted with toluene to 8 ml was injected and the injector system was rinsed twice with about 8 ml toluene) and the stirring at 800 rpm was continued for 30 minutes.

The Cr-catalyst system prepared as described above was introduced into the stirred reactor using an injection system with the aid of toluene (the total volume injected was about 25 ml: the catalyst solution diluted with toluene to 8 ml was injected and the injector system was rinsed twice with about 8 ml toluene). The initial loading of the reactor was about 300 ml.

The addition of the catalyst system resulted, after an induction period of about 5 minutes, in an exotherm (generally some 5-10° C.), which generally reached a maximum within 1 minute and was followed by establishment of the temperature of 40° C. and the pressure of 15 or 30 barg as indicated in Table 1.

After consuming the desired volume of ethylene, the simultaneous tri- and tetramerization was stopped by rapid cooling to room temperature (in about 5 minutes), followed by venting of the ethylene, decanting the product mixture into a collection bottle using a tap in the base of the autoclave. Exposure of the mixture to air resulted in rapid deactivation of the catalyst.

After addition of n-hexylbenzene (0.5-3.5 g) as internal standard to the crude product, the amount of the $C_4$-$C_{30}$ olefins and purity of $C_6$, $C_8$ and $C_{10}$ olefins was determined by gas chromatography. The experimental data is reported in Table 1.

In the case of experiments under 30 barg of ethylene pressure a 0.5-litre steel autoclave, equipped similarly to the above-described 1.0-litre autoclave, was used, loaded with a total of 150 ml of toluene, MAO-solution and Cr-catalyst system. The amounts of the Cr-catalyst system, MAO-solution, solvent and ethylene consumption were typically half of those used in the corresponding 1.0-litre experiments in order to maintain an Al/Cr atomic ratio of about 200:1 and a final alpha olefin concentration similar to that of the experiments performed at 15 barg.

The experimental data is provided in Table 1 below.

TABLE 1

| Example | Cr (µmol) | Ligand (mol$_{lig}$)/(mol$_{cr}$) | Cr Source | Temperature (°C.) | Pressure (barg) | Time (min) | TOF (TON)† | C$_6$ (% wt) |
|---|---|---|---|---|---|---|---|---|
| 1 | 18 | B'/C (1/1.0) (1) | CrCl$_3$ | 40 | 15 | 32 | 214 (114) | 83.9 |
| 2 | 8 | B'/C (1/1.1) (1) | CrCl$_3$ | 40 | 30 | 119 | 75 (150) | 71.4 |
| 3 | 31 | B/C (0.9/0.3) (1) | Cr(acac)$_3$ | 40 | 15 | 230 | 15 (58) | 78.2 |
| 4 | 8 | B'/D (1/1.1) (1) | CrCl$_3$ | 40 | 30 | 17 | 484 (137) | 74.8 |
| 5# | 31 | A'/C (1/1.1) (1) | CrCl$_3$ | 40 | 15 | 150 | 25 (62) | 67.4 |
| 6# | 33 | A/C (0.6/0.6) (1) | Cr(acac)$_3$ | 40 | 15 | 40 | 96 (64) | 59.0 |
| 7# | 33 | A/C (0.9/0.3) (1) | Cr(acac)$_3$ | 40 | 15 | 24 | 160 (64) | 65.7 |
| 8# | 29 | C (1.1) (1) | Cr(acac)$_3$ | 40 | 15 | 120 | 16 (32) | 22.4 |
| 9# | 30 | A' (1) (1) | CrCl$_3$ | 40 | 15 | 30 | 180 (90) | 67.3 |
| 10# | 15 | B' (1) (1) | CrCl$_3$ | 40 | 15 | 10 | 1190 (199) | 85.2 |
| 11# | 15 | D (1.1) (1) | Cr(acac)$_3$ | 40 | 30 | 23 | 188 (72) | 37.7 |

| Example | 1-C$_6$‡ (% wt) | C$_8$ (% wt) | 1-C$_8$* (% wt) | C$_{10}$** (% wt) | C$_{12}$-C$_{14}$ (% wt) | Solids (g); (% wt) | Total Product (g) | 1-C$_6$ + 1-C$_8$ on Total % wt |
|---|---|---|---|---|---|---|---|---|
| 1 | 99.4 | 10.4 | 99.3 | 4.5 | 1.1 | <0.05 (<0.1) | 56.2 | 93.7 |
| 2 | 98.9 | 22.1 | 99.3 | 3.9 | 1.4 | 0.23 (0.7) | 33.4 | 92.5 |
| 3 | 99.0 | 15.6 | 99.5 | 4.1 | 1.1 | 0.05 (0.1) | 50.2 | 92.9 |
| 4 | 99.6 | 18.6 | 99.4 | 4.3 | 1.6 | 0.16 (0.5) | 29.5 | 93.0 |
| 5# | 98.8 | 9.2 | 99.1 | 18.9 | 4.0 | 0.1 (0.2) | 53.3 | 75.7 |
| 6# | 97.0 | 21.0 | 99.0 | 15.2 | 4.4 | 0.05 (<0.1) | 58.1 | 78.0 |
| 7# | 98.4 | 11.9 | 99.0 | 17.8 | 3.9 | 0.05 (<0.1) | 58.4 | 76.4 |
| 8# | 79.4 | 69.2 | 99.1 | 1.4## | 3.6 | 0.3 (1.1) | 27.0 | 86.4 |
| 9# | 99.1 | 6.4 | 98.7 | 21.5 | 4.3 | 0.1 (0.1) | 75.6 | 73.0 |
| 10# | 99.8 | 2.9 | >99.8 | 11.0 | 0.9 | <0.05 (<0.1) | 84.7 | 87.9 |
| 11# | 97.0 | 46.7 | 98.8 | 5.8 | 8.4 | 0.04 (0.1) | 30.3 | 82.7 |

†Turnover frequency, TOF in hourly kmol converted ethylene/mol catalyst (kmol/mol · h); turnover number, TON in kmol converted ethylene/mol catalyst (kmol/mol).
‡% of 1-hexene by weight of the C$_6$ portion of the product composition.
*% of 1-octene by weight of the C$_8$ portion of the product composition.
**Predominantly branched and/or internal decenes, unless indicated differently.
Comparative example.
About 50% of 1-decene by weight of the C$_{10}$ portion of the product composition.
C$_6$ Hydrocarbons containing 6 carbon atoms; 1-C$_6$ is 1-hexene.
C$_8$ Hydrocarbons containing 8 carbon atoms; 1-C$_8$ is 1-octene.
C$_{10}$ Hydrocarbons containing 10 carbon atoms.
C$_{12}$-C$_{14}$ Hydrocarbons containing 12 and/or 14 carbon atoms.
Solids: The amount of heavy olefin wax and polyethylene isolated by filtration.
Total Product: The amount of C$_4$-C$_{100}$ olefins, derived from GC analysis, including the amount of solids.

It can be seen from Table 1 that the use of a Cr[III] catalyst composition according to the present invention result in good yields of mixtures of high purity 1-hexene and 1-octene (at least 92.5 wt % on total product for Examples 1 to 4) with low solids formation (0.7% wt or less on total product for Examples 1 to 4), low $C_{10}$ formation (4.5% wt or less on total product for Examples 1 to 4) and low $C_{12}$ to $C_{14}$ formation (1.6% wt or less on total product for Examples 1 to 4).

What is claimed is:

1. A catalyst precursor composition comprising:
   a) a source of chromium, molybdenum or tungsten;
   b) a first ligand having the general formula (I);

$$(R^1)(R^2)P—X—P(R^3)(R^4) \qquad (I)$$

wherein:
   X is a bridging group of the formula —N($R^5$)—, wherein $R^5$ is selected from hydrogen, a hydrocarbyl group, a substituted hydrocarbyl group, a heterohydrocarbyl group, a substituted heterohydrocarbyl group, a silyl group or derivative thereof;
   at least three of $R^1$ to $R^4$ are independently selected from optionally substituted aromatic groups, each bearing a polar substituent on at least one of the ortho-positions; and
   optionally one of $R^1$ to $R^4$ is independently selected from hydrocarbyl, substituted hydrocarbyl, heterohydrocarbyl and substituted heterohydrocarbyl groups with the proviso that when the group is aromatic it does not contain a polar substituent at any of the ortho-positions;
   c) a second ligand having the general formula (II);

$$(R^{1'})(R^{2'})P—X'—P(R^{3'})(R^{4'}) \qquad (II)$$

wherein:
   X' is a bridging group as defined for X of the first ligand, component (b), of general formula (I);
   at least $R^{1'}$ and $R^{2'}$ of $R^{1'}$ to $R^{4'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions; and
   none, one or both of $R^{3'}$ and $R^{4'}$ are independently selected from an optionally substituted aromatic group bearing a polar substituent on at least one of the ortho-positions.

2. The catalyst precursor composition of claim 1 wherein $R^5$ is selected from $C_1$-$C_{15}$ alkyl groups, substituted $C_1$-$C_{15}$ alkyl groups, $C_2$-$C_{15}$ alkenyl groups, substituted $C_2$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups, preferably $C_1$-$C_{15}$ alkyl groups.

3. The catalyst precursor composition of claim 1 wherein all four of $R^1$ to $R^4$ are independently selected from optionally substituted aromatic groups, each bearing a polar substituent on at least one of the ortho-positions.

4. The catalyst precursor composition of claim 3 wherein each of the $R^1$ to $R^4$ groups are the same and bear the same number and type of polar substituents.

5. The catalyst precursor composition of claim 1 wherein each of said $R^1$ to $R^4$ bears a polar substituent on only one of their two ortho-positions.

6. The catalyst precursor composition of claim 5 wherein the polar substituents are o-anisyl.

7. The catalyst precursor composition of claim 1 wherein at least three of $R^1$ to $R^4$ are o-anisyl.

8. The catalyst precursor composition of claim 1 wherein $R^{1'}$ and $R^{2'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions.

9. The catalyst precursor composition of claim 1 wherein all four of $R^{1'}$ to $R^{4'}$ are independently selected from hydrocarbyl, substituted hydrocarbyl, heterohydrocarbyl and substituted heterohydrocarbyl groups with the proviso that when the group is aromatic it does not contain a polar substituent at any of the ortho-positions.

10. The catalyst precursor composition of claim 1 wherein at least $R^{1'}$ and $R^{2'}$ are independently selected from unsubstituted or substituted aromatic groups which do not contain a polar substituent at any of the ortho-positions.

11. The catalyst precursor composition of claim 1 wherein the source of chromium, molybdenum or tungsten, (a) is a source of chromium.

12. The catalyst precursor composition of claim 11 wherein the source of chromium is selected from chromium tris(2,4-pentanedionate), Cr(acac)$_3$, chromium trichloride, CrCl$_3$, and chromium trichloride tris-tetrahydrofuran complex, CrCl$_3$(THF)$_3$.

13. A catalyst system comprising the catalyst precursor composition of claim 1 which additionally comprises component (d) a cocatalyst.

14. The catalyst system of claim 13 wherein the cocatalyst, component (d), is selected from methylaluminoxane and modified methylaluminoxane.

* * * * *